United States Patent [19]

Frickel et al.

[11] Patent Number: 4,578,498

[45] Date of Patent: Mar. 25, 1986

[54] PHENYLETHYLENE DERIVATIVES AND THEIR USE AS DRUGS

[75] Inventors: Fritz-Frieder Frickel, Deidesheim; Axel Nuerrenbach, Gruenstadt, both of Fed. Rep. of Germany

[73] Assignee: BASF Aktiengesellschaft, Fed. Rep. of Germany

[21] Appl. No.: 515,465

[22] Filed: Jul. 20, 1983

Related U.S. Application Data

[63] Continuation-in-part of Ser. No. 457,182, Jan. 11, 1983, abandoned.

[30] Foreign Application Priority Data

Jan. 23, 1982 [DE] Fed. Rep. of Germany ....... 3202100

[51] Int. Cl.$^4$ ........................................... C07C 69/76
[52] U.S. Cl. ....................................... 560/8; 560/100; 562/405; 514/532; 514/569
[58] Field of Search ................ 562/405, 490; 560/100, 560/8

[56] References Cited

U.S. PATENT DOCUMENTS 4,326,055 4/1982 Loelifer ............................... 562/490

OTHER PUBLICATIONS

Chem. Abstr. 96, 141529y (1982).

Primary Examiner—Paul J. Killos
Attorney, Agent, or Firm—Keil & Weinkauf

[57] ABSTRACT

Phenylethylene derivatives of the formula

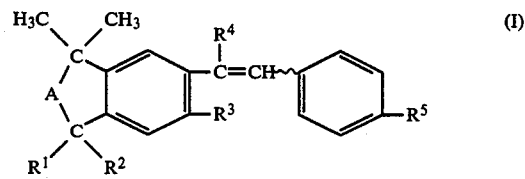

where $R^1$, $R^2$, $R^3$, $R^4$, $R^5$ and A have the meanings given in the description, and their preparation.

The novel compounds are useful for combating disorders.

11 Claims, No Drawings

PHENYLETHYLENE DERIVATIVES AND THEIR USE AS DRUGS

This application is a continuation-in-part of application Ser. No. 457,182 filed Jan. 11, 1983 now abandoned.

The present invention relates to phenylethylene derivatives, processes for their preparation, and therapeutic agents containing these compounds and their use in combating disorders.

German Laid-Open Application DOS No. 2,854,354 discloses that stilbene derivatives have pharmacological actions when used for topical and systemic therapy of neoplasms, acne, psoriasis and other dermatological disorders. However, the pronounced toxic effect or side effect of these compounds is particularly disadvantageous, and renders them substantially unsuitable as agents for the topical and systemic therapy of the above disorders. The disadvantageous effect of the stilbene derivatives of German Laid-Open Application DOS No. 2,854,354 is described by, for example, A. Kistler in Calcified Tissue International 33, (1981), 249–254, and is evident in particular in repeated systemic administration to rodents by the method published by R. C. Moon et al [Cancer Research 39, (1979), 1339–1346] or in repeated topical administration to rodents.

It is an object of the present invention to provide compounds having a comparable intensity of action but less pronounced toxic side effects.

We have found that this object is achieved by phenylethylene derivatives of the formula

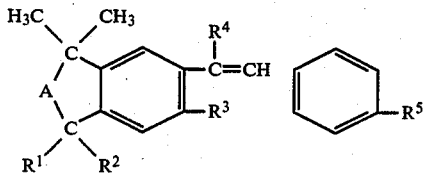

I where A is $C_1-C_2$-alkylene which is unsubstituted or substituted by $C_1-C_4$-alkyl, $R^1$ is hydrogen or methyl, $R^2$ is hydrogen or methyl, $R^3$ is hydrogen or $C_1-C_{16}$-alkyl, $R^4$ is hydrogen or $C_1-C_4$-alkyl and $R^5$ is p-hydroxyphenyleneaminocarbonyl or tetrazol-5-ylaminocarbonyl and, if $R^3$ is $C_1-C_{16}$-alkyl, may furthermore be carboxyl or $C_2-C_4$-carbalkoxy, and, where relevant, their salts with physiologically tolerated bases.

A is preferably an unsubstituted or methyl-substituted methylene or ethylene group. More preferable A is a methyl-substituted ethylene group. $R^3$ is preferably hydrogen or a $C_1-C_{12}$-alkyl, more preferably hydrogen or $C_{1-8}$-alkyl.

The C—C bond represented by a wavy line can be either above or below the plane of the paper, and accordingly belong to a cis (Z) or a trans (E) compound.

Typical examples of novel compounds are especially the following compounds in their Z or E configuration:
ethyl 4-[2-methyl-2-(1,1,4,4,6-pentamethyl-1,2,3,4-tetrahydronaphth-7-yl)-vinyl]-benzoate,
4-[2-methyl-2-(1,1,4,4,6-pentamethyl-1,2,3,4-tetrahydronaphth-7-yl)-vinyl]-benzoic acid,
4-[2-methyl-2-(1,1,6-trimethyl-1,2,3,4-tetrahydronaphth-7-yl)-vinyl]-benzoic acid,
ethyl 4-[2-methyl-2-(1,1,6-trimethyl-1,2,3,4-tetrahydronaphth-7-yl)-vinyl]-benzoate,
ethyl 4-[2-ethyl-2-(1,1,4,4,6-pentamethyl-1,2,3,4-tetrahydronaphth-7-yl)-vinyl]-benzoate,
4-[2-ethyl-2-(1,1,4,4,6-pentamethyl-1,2,3,4-tetrahydronaphth-7-yl)-vinyl]-benzoic acid,
ethyl 4-[2-methyl-2-(1,1,4,4-tetramethyl-6-ethyl-1,2,3,4-tetrahydronaphth-7-yl)-vinyl]-benzoate,
4-[2-methyl-2-(1,1,4,4-tetramethyl-6-ethyl-1,2,3,4-tetrahydronaphth-7-yl)-vinyl]-benzoic acid,
4-[2-methyl-2-(1,1,4,4-tetramethyl-6-isopropyl-1,2,3,4-tetrahydronaphth-7-yl)-vinyl]-benzoic acid,
ethyl 4-[2-methyl-2-(1,1,4,4-tetramethyl-6-isopropyl-1,2,3,4-tetrahydronaphth-7-yl)-vinyl]-benzoate,
4-[2-methyl-2-(1,1,4,4-tetramethyl-6-propyl-1,2,3,4-tetrahydronaphth-7-yl)-vinyl]-benzoic acid,
ethyl 4-[2-methyl-2-(1,1,4,4-tetramethyl-6-propyl-1,2,3,4-tetrahydronaphth-7-yl)-vinyl]-benzoate,
methyl 4-[2-methyl-2-(1,1,4,4-tetramethyl-6-butyl-1,2,3,4-tetrahydronaphth-7-yl)-vinyl]-benzoate,
ethyl 4-[2-methyl-2-(1,1,4,4-tetramethyl-6-butyl-1,2,3,4-tetrahydronaphth-7-yl)-vinyl]-benzoate,
4-[2-methyl-2-(1,1,4,4-tetramethyl-6-butyl-1,2,3,4-tetrahydronaphth-7-yl)-vinyl]-benzoic acid,
ethyl 4-[2-methyl-2-(1,1,4,4-tetramethyl-6-(2-methylpropyl)-1,2,3,4-tetrahydronaphth-7-yl)-vinyl]-benzoate,
4-[2-methyl-2-(1,1,4,4-tetramethyl-6-(2-methylpropyl)-1,2,3,4-tetrahydronaphth-7-yl)-vinyl]-benzoic acid,
ethyl 4-[2-methyl-2-(1,1,3,4,4,6-hexamethyl-1,2,3,4-tetrahydronaphth-7-yl)-vinyl]-benzoate,
4-[2-methyl-2-(1,1,3,4,4,6-hexamethyl-1,2,3,4-tetrahydronaphth-7-yl)-vinyl]-benzoic acid,
ethyl 4-[2-methyl-2-(1,1,2,3,3,5-hexamethylindan-6-yl)-vinyl]-benzoate,
propyl 4-[2-methyl-2-(1,1,2,3,3,5-hexamethylindan-6-yl)-vinyl]-benzoate,
isopropyl 4-[2-methyl-2-(1,1,2,3,3,5-hexamethylindan-6-yl)-vinyl]-benzoate,
4-[2-methyl-2-(1,1,2,3,3,5-hexamethylindan-6-yl)-vinyl]-benzoic acid,
4-[2-methyl-2-(1,1,3,3,5-pentamethylindan-6-yl)-vinyl]-benzoic acid,
methyl 4-[2-methyl-2-(1,1,3,3,5-pentamethylindan-6-yl)-vinyl]-benzoate,
ethyl 4-[2-methyl-2-(1,1,3,3,5-pentamethylindan-6-yl)-vinyl]-benzoate,
methyl 4-[2-methyl-2-(1,1,4,4,6-pentamethyl-1,2,3,4-tetrahydronaphth-7-yl)-vinyl]-benzoate,
propyl 4-[2-methyl-2-(1,1,4,4,6-pentamethyl-1,2,3,4-tetrahydronaphth-7-yl)-vinyl]-benzoate,
ethyl 4-[2-ethyl-2-(1,1,4,4,6-pentamethyl-1,2,3,4-tetrahydronaphth-7-yl)-vinyl]-benzoate,
4-[2-ethyl-2-(1,1,4,4,6-pentamethyl-1,2,3,4-tetrahydronaphth-7-yl)-vinyl]-benzoic acid,
methyl 4-[2-ethyl-2-(1,1,4,4,6-pentamethyl-1,2,3,4-tetrahydronaphth-7-yl)-vinyl]-benzoate,
4-[2-methyl-2-(1,1,4,4-tetramethyl-6-n-butyl-1,2,3,4-tetrahydronaphth-7-yl)-vinyl]-benzoic acid,
4-[2-methyl-2-(1,1,4,4-tetramethyl-6-n-octyl-1,2,3,4-tetrahydronaphth-7-yl)-vinyl]-benzoic acid,
4-[2-methyl-2-(1,1,6-trimethyl-1,2,3,4-tetrahydronaphth-7-yl)-vinyl]-benzoic acid,
butyl 4-[2-methyl-2-(1,1,4,4,6-pentamethyl-1,2,3,4-tetrahydronaphth-7-yl)-vinyl]-benzoate
4-[2-(1,1,4,4,6-pentamethyl-1,2,3,4-tetrahydronaphth-7-yl)-vinyl]-benzoic acid
methyl 4-[2-(1,1,4,4,6-pentamethyl-1,2,3,4-tetrahydronaphth-7-yl)-vinyl]-benzoate ethyl 4-[2-(1,1,4,4,6-pentamethyl-1,2,3,4-tetrahydronaphth-7-yl)-vinyl]-benzoate
propyl 4-[2-methyl-2-(1,1,3,3,5-pentamethylindan-6-yl)-vinyl]-benzoate
butyl 4-[2-methyl-2-(1,1,3,3,5-pentamethylindan-6-yl)-vinyl]-benzoate 4-[2-(1,1,3,3,5-pentamethylindan-6-yl)-vinyl]-benzoic acid ethyl 4-[2-(1,1,3,3,5-pentamethylindan-6-yl)-vinyl]-benzoate
methyl 4-[2-(1,1,3,3,5-pentamethylindan-6-yl)-vinyl]-benzoate
4-[2-methyl-2-(1,1,3,3-tetramethyl-5-ethylindan-6-yl)-vinyl]-benzoic acid
4-[2-methyl-2-(1,1,2,3,3-pentamethyl-5-ethyl-indan-6-yl)-vinyl]-benzoic acid
methyl 4-[2-methyl-2-(1,1,4,4-tetramethyl-6-ethyl-1,2,3,4-tetrahydronaphth-7-yl)-vinyl]-benzoate
propyl 4-[2-methyl-2-(1,1,4,4-tetramethyl-6-ethyl-1,2,3,4-tetrahydronaphth-7-yl)-vinyl]-benzoate
butyl 4-[2-methyl-2-(1,1,4,4-tetramethyl-6-ethyl-1,2,3,4-tetrahydronaphth-7-yl)-vinyl]-benzoate
isopropyl 4-[2-methyl-2-(1,1,4,4-tetramethyl-6-ethyl-1,2,3,4-tetrahydronaphth-7-yl)-vinyl]-benzoate
4-[2-(1,1,4,4-tetramethyl-6-ethyl-1,2,3,4-tetrahydronaphth-7-yl)-vinyl]-benzoic acid
ethyl 4-[2-(1,1,4,4-tetramethyl-6-ethyl-1,2,3,4-tetrahydronaphth-7-yl)-vinyl]-benzoate
methyl 4-[2-(1,1,4,4-tetramethyl-6-ethyl-1,2,3,4-tetrahydronaphth-7-yl)-vinyl]-benzoate
methyl 4-[2-methyl-2-(1,1,3,3-tetramethlyl-5-ethyl-indan-6-yl)-vinyl]-benzoate
ethyl 4-[2-methyl-2-(1,1,3,3-tetramethyl-5-ethyl-indan-6-yl)-vinyl]-benzoate
propyl 4-[2-methyl-2-(1,1,3,3-tetramethyl-5-ethyl-indan-6-yl)-vinyl]-benzoate
methyl 4-[2-methyl-2-(1,1,2,3,3-pentamethyl-5-ethyl-indan-6-yl)-vinyl]-benzoate
ethyl 4-[2-methyl-2-(1,1,2,3,3-pentamethyl-5-ethyl-indan-6-yl)-vinyl]-benzoate
methyl 4-[2-methyl-2-(1,1,4,4-tetramethyl-6-isopropyl-1,2,3,4-tetrahydronaphth-7-yl)-vinyl]-benzoate
methyl 4-[2-methyl-2-(1,1,4,4-tetramethyl-6-propyl-1,2,3,4-tetrahydronaphth-7-yl)-vinyl]-benzoate
propyl 4-[2-methyl-2-(1,1,4,4-tetramethyl-6-propyl-1,2,3,4-tetrahydronaphth-7-yl)-vinyl]-benzoate
4-[2-methyl-2-(1,1,3,3-tetramethyl-5-propyl-indan-6-yl)-vinyl]-benzoic acid
4-[2-methyl-2-(1,1,2,3,3-pentamethyl-5-propyl-indan-6-yl)-vinyl]-benzoic acid
4-[2-(1,1,3,3-tetramethyl-5-propyl-indan-6-yl)-vinyl]-benzoic acid
4-[2-(1,1,2,3,3-pentamethyl-5-propyl-indan-6-yl)-vinyl]-benzoic acid
methyl 4-[2-methyl-2-(1,1,3,3-tetramethyl-5-propyl-indan-6-yl)-vinyl]-benzoate
ethyl 4-[2-methyl-2-(1,1,3,3-tetramethyl-5-propyl-indan-6-yl)-vinyl]-benzoate
methyl 4-[2-methyl-2-(1,1,2,3,3-pentamethyl-5-propyl-indan-6-yl)-vinyl]-benzo
ethyl 4-[2-methyl-2-(1,1,2,3,3-pentamethyl-5-propyl-indan-6-yl)-vinyl]-benzoate
propyl 4-[2-methyl-2-(1,1,4,4-tetramethyl-6-butyl-1,2,3,4-trtrahydronaphth-7-yl)-vinyl]-benzoate
4-[2-methyl-2-(1,1,3,3-tetramethyl-5-butyl-indan-6-yl)-vinyl]-benzoic acid
4-[2-methyl-2-(1,1,2,3,3-pentamethyl-5-butyl-indan-6-yl)-vinyl]-benzoic acid
methyl 4-[2-methyl-2-(1,1,3,3-tetramethyl-5-butyl-indan-6-yl)-vinyl]-benzoate
ethyl 4-[2-methyl-2-(1,1,3,3-tetramethyl-5-butyl-indan-6-yl)-benzoate
propyl 4-[2-methyl-2-(1,1,3,3-tetramethyl-5-butyl-indan-6-yl)-vinyl]-benzoate
methyl 4-[2-methyl-2-(1,1,2,3,3-pentamethyl-5-butyl-indan-6-yl)-vinyl]-benzoate
ethyl 4-[2-methyl-2-(1,1,2,3,3-pentamethyl-5-butyl-indan-6-yl)-vinyl]-benzoate
propyl 4-[2-methyl-2-(1,1,2,3,3-pentamethyl-5-butyl-indan-6-yl)-vinyl]-benzoate
methyl 4-[2-methyl-2-(1,1,4,4-tetramethyl-6-(2-methyl-propyl)-1,2,3,4-tetrahhydronaphth-7-yl)-vinyl]-benzoate
propyl 4-[2-methyl-2-(1,1,4,4-tetramethyl-6-(2-methylpropyl)-1,2,3,4-tetrahydronaphth-7-yl)-vinyl]-benzoate
isopropyl 4-[2-methyl-2-(1,1,4,4-tetramethyl-6-(2-methylpropyl)-1,2,3,4-tetrahydronaphth-7-yl)-vinyl]-benzoate
butyl 4-[2-methyl-2-(1,1,4,4-tetramethyl-6-(2-methylpropyl)-1,2,3,4-tetrahydronaphth-7-yl)-vinyl]-benzoate
4-[2-methyl-2-(1,1,4,4-tetramethyl-6-(2-methylpropyl)-1,2,3,4-tetrahydronaphth-7-yl)-vinyl]-benzoic acid sodium salt
4-[2-methyl-2-(1,1,3,3-tetramethyl-5-(2-methylpropyl)-indan-6-yl)-vinyl]-benzoic acid
4-[2-methyl-2-(1,1,2,3,3-pentamethyl-5-(2-methylpropyl)-indan-6-yl)-vinyl]-benzoic acid
methyl 4-[2-methyl-2-(1,1,3,3-tetramethyl-5-(2-methylpropyl)-indan-6-yl)-vinyl]-benzoate
ethyl 4-[2-methyl-2-(1,1,3,3-tetramethyl-5-(2-methylpropyl)-indan-6-yl)-vinyl]-benzoate
propyl 4-[2-methyl-2-(1,1,3,3-tetramethyl-5-(2-methylpropyl)-indan-6-yl)-vinyl]-benzoate
butyl 4-[2-methyl-2-(1,1,3,3-tetramethyl-5-(2-methylpropyl)-indan-6-yl)-vinyl]-benzoate
isopropyl 4-[2-methyl-2-(1,1,3,3-tetramethyl-5-(2-methylpropyl)-indan-6-yl)-vinyl]-benzoate
methyl 4-[2-methyl-2-(1,1,2,3,3-pentamethyl-5-(2-methylpropyl)-indan-6-yl)-vinyl]-benzoate
ethyl 4-[2-methyl-2-(1,1,2,3,3-pentamethyl-5-(2-methylpropyl)-indan-6-yl)-vinyl]benzoate
propyl 4-[2-methyl-2-(1,1,2,3,3-pentamethyl-5-(2-methylpropyl)-indan-6-yl)-vinyl]-benzoate
butyl 4-[2-methyl-2-(1,1,2,3,3-pentamethyl-5-(2-methylpropyl)-indan-6-yl)-vinyl]-benzoate
isopropyl -4-[2-methyl-2-(1,1,2,3,3-pentamethyl-5-(2-methylpropyl)-indan-6-yl)-vinyl]-benzoate
4-[2-(1,1,4,4-tetramethyl-6-(2-methyl-propyl)-1,2,3,4-tetrahydronaphth-7-yl)-vinyl]-benzoic acid
methyl 4-[2-(1,1,4,4-tetramethyl-6-(2-methylpropyl)-1,2,3,4-tetrahydronaphth-7-yl)-vinyl]-benzoate
ethyl 4-[2-(1,1,4,4-tetramethyl-6-(2-methylpropyl)-1,2,3,4-tetrahydronaphth-7-yl)-vinyl]-benzoate
4-[2-ethyl-2-(1,1,4,4-tetramethyl-6-(2-methylpropyl)-1,2,3,4-tetrahydronaphth-7-yl)-vinyl]-benzoic acid
methyl 4-[2-ethyl-2-(1,1,4,4-tetramethyl-6-(2-methylpropyl)-1,2,3,4-tetrahydronaphth-7-yl)-vinyl]-benzoate
ethyl 4-[2-ethyl-2-(1,1,4,4-tetramethyl-6-(2-methylpropyl)-1,2,3,4-tetrahydronaphth-7-yl)-vinyl]-benzoate
4-[2-methyl-2-(1,1,4,4-tetramethyl-6-pentyl-1,2,3,4-tetrahydronaphth-7-yl)-vinyl]-benzoic acid
4-[2-methyl-2-(1,1,4,4-tetramethyl-6-hexyl-1,2,3,4-tetrahydronaphth-7-yl)-vinyl]benzoic acid 4-[2-methyl-2-(1,1,4,4-tetramethyl-6-heptyl-1,2,3,4-tetrahydronaphth-7-yl)-vinyl]-benzoic acid
methyl 4-[2-methyl-2-(1,1,4,4-tetramethyl-6-octyl-1,2,3,4-tetrahydronaphth-7-yl)-vinyl]-benzoate
ethyl 4-[2-methyl-2-(1,1,4,4-tetramethyl-6-octyl-1,2,3,4-tetrahydronaphth-7-yl)-vinyl]-benzoate
methyl 4-[2-methyl-2-(1,1,4,4-tetramethyl-6-pentyl-1,2,3,4-tetrahydronaphth-7-yl)-vinyl]-benzoate
ethyl 4-[2-methyl-2-(1,1,4,4-tetramethyl-6-pentyl-1,2,3,4-tetrahydronaphth-7-yl)-vinyl]-benzoate
methyl 4-[2-methyl-2-(1,1,4,4-tetramethyl-6-hexyl-1,2,3,4-tetrahydronaphth-7-yl)-vinyl]-benzoate
ethyl 4-[2-methyl-2-(1,1,4,4-tetramethyl-6-hexyl-1,2,3,4-tetrahydronaphth-7-yl)-vinyl]-benzoate
methyl 4-[2-methyl-2-(1,1,4,4-tetramethyl-6-heptyl-1,2,3,4-tetrahhydronaphth-7-yl)-vinyl]-benzoate
ethyl 4-[2-methyl-2-(1,1,4,4-tetramethyl-6-heptyl-1,2,3,4-tetrahydronaphth-7-yl)-vinyl]-benzoate
4-[2-(1,1,4,4-tetramethyl-6-butyl-1,2,3,4-tetrahydronaphth-7-yl)-vinyl]-benzoic acid
4-[2-(1,1,4,4-tetramethyl-6-pentyl-1,2,3,4-tetrahydronaphth-7-yl)-vinyl]-benzoic acid
4-[2-(1,1,4,4-tetramethyl-6-hexyl-1,2,3,4-tetrahydronaphth-7-yl)-vinyl]-benzoic acid
4-[2-(1,1,4,4-tetramethyl-6-heptyl-1,2,3,4-tetrahydronaphth-7-yl)-vinyl]-benzoic acid
4-[2-(1,1,4,4-tetramethyl-6-octyl-1,2,3,4-tetrahydronaphth-7-yl)-vinyl]-benzoic acid
methyl 4-[2-(1,1,4,4-tetramethyl-6-butyl-1,2,3,4-tetrahydronaphth-7-yl)-vinyl]-benzoate
methyl 4[2-1,1,4,4-tetramethyl-6-pentyl-1,2,3,4-tetrahydronaphth-7-yl)-vinyl]-benzoate
methyl 4-[2-(1,1,4,4-tetramethyl-6-hexyl-1,2,3,4-tetrahydronaphth-7-yl)-vinyl]-benzoate
methyl 4-[2-(1,1,4,4-tetramethyl-6-heptyl-1,2,3,4-tetrahydronaphth-7-yl)-vinyl]-benzoate
methyl 4-[2-(1,1,4,4-tetramethyl-6-octyl-1,2,3,4-tetrahydronaphth-7-yl)-vinyl]-benzoate
4-[2-ethyl-2-(1,1,4,4-tetramethyl-6-octyl-1,2,3,4-tetrahydronaphth-7-yl)-vinyl]-benzoic acid
methyl 4-[2-ethyl-2-(1,1,4,4-tetramethyl-6-octyl-1,2,3,4-tetrahydronaphth-7-yl)-vinyl]-benzoate
4-[2-methyl-2-(1,1,3,3-tetramethyl-5-pentyl-indan-6-yl)-vinyl]-benzoic acid
4-[2-methyl-2-(1,1,2,3,3-pentamethyl-5-pentyl-indan-6-yl)-vinyl]-benzoic acid
methyl 4-[2-methyl-2(1,1,3,3-tetramethyl-5-pentyl-indan-6-yl)-vinyl]-benzoate
methyl 4-[2-methyl-2-(1,1,2,3,3-pentamethyl-5-pentyl-indan-6-yl)-vinyl]-benzoate
4-[2-methyl-2-(1,1,3,3-tetramethyl-5-hexyl-indan-6-yl)-vinyl]-benzoic acid
4-[2-methyl-2-(1,1,2,3,3-pentamethyl-5-hexyl-indan-6-yl)-vinyl]-benzoic acid
methyl 4-[2-methyl-2-(1,1,3,3-tetramethyl-5-hexyl-indan-6-yl)-vinyl]-benzoate
methyl 4-[2-methyl-2-(1,1,2,3,3-pentamethyl-5-hexyl-indan-6-yl)-vinyl]-benzoate
4-[2-methyl-2-(1,1,3,3-tetramethyl-5-heptyl-indan-6-yl)-vinyl]-benzoic acid
methyl 4-[2-methyl-2-(1,1,2,3,3-pentamethyl-5-heptyl-indan-6-yl)-vinyl]-benzoate
4-[2-methyl-2-(1,1,2,3,3-pentamethyl-5-heptyl-indan-6-yl)-vinyl]-benzoic acid
methyl 4-[2-methyl-2-(1,1,2,3,3-pentamethyl-5-heptyl-indan-6-yl)-vinyl]-benzoate
4-[2-methyl-2-(1,1,3,3-tetramethyl-5-octyl-indan-6-yl)-vinyl]-benzoic acid
4-[2-methyl-2-(1,1,2,3,3-pentamethyl-5-octyl-indan-6-yl)-vinyl]-benzoic acid
methyl 4-[2-methyl-2-(1,1,2,3,3-pentamethyl-5-octyl-indan-6-yl)-vinyl]-benzoate
methyl 4-[2-methyl-2-(1,1,3,3-tetramethyl-5-octyl-indan-6-yl)-vinyl]-benzoate
4-[2-methyl-2-(1,1,3,3-tetramethyl-5-(3-methylbutyl)-indan-6-yl)-vinyl]-benzoic acid
4-[2-methyl-2-(1,1,2,3,3-pentamethyl-5-(3-methylbutyl)-indan-6-yl)-vinyl]-benzoic acid
4-[2-methyl-2-(1,1,4,4-tetramethyl-6-(3-methylbutyl)-1,2,3,4-tetrahydronaphth-7-yl)-vinyl]-benzoic acid
4-[2-methyl-2-(1,1,3,3-tetramethyl-5-(3-methylpentyl)-indan-6-yl)-vinyl]-benzoic acid
4-[2-methyl-2-(1,1,2,3,3-pentamethyl-5-(3-methylpentyl)-indan-6-yl)-vinyl]-benzoic acid
4-[2-methyl-2-(1,1,4,4-tetramethyl-6-(3-methylpentyl)-1,2,3,4-tetrahydronaphth-7-yl)-vinyl]-benzoic acid
4-[2-methyl-2-(1,1,3,3-tetramethyl-5-(3-ethylpentyl)-indan-6-yl)-vinyl]-benzoic acid
4-[2-methyl-2-(1,1,2,3,3-pentamethyl-5-(3-ethylpentyl)-indan-6-yl)-vinyl]-benzoic acid
4-[2-methyl-2-(1,1,4,4-tetramethyl-6-(3-ethylpentyl)-1,2,3,4-tetrahydronaphth-7-yl)-vinyl]-benzoic acid
methyl 4-[2-methyl-2-(1,1,3,3-tetramethyl-5-(3-methylbutyl)-indan-6-yl)-vinyl]-benzoate
methyl 4-[2-methyl-2-(1,1,2,3,3-pentamethyl-5-(3-methylbutyl)-indan-6-yl)-vinyl]-benzoate
methyl 4-[2-methyl-2-(1,1,4,4-tetramethyl-6-(3-ethylpentyl)-1,2,3,4-tetrahydronaphth-7-yl)-vinyl]-benzoate
4-[2-(1,1,3,3-tetramethyl-5-(3-methylbutyl)-indan-6-yl)-vinyl]-benzoic acid
methyl 4-[2-(1,1,3,3-tetramethyl-5-(3-methylbutyl)-indan-6-yl)-vinyl]-benzoate
4-[2-(1,1,2,3,3-pentamethyl-5-(3-methylbutyl)-indan-6-yl)-vinyl]-benzoic acid
methyl 4-[2-(1,1,2,3,3-pentamethyl-5-(3-methylbutyl)-indan-6-yl)-vinyl]-benzoate
4-[2-(1,1,4,4-tetramethyl-6-(3-methylbutyl)-1,2,3,4-tetrahydronaphth-7-yl)-vinyl]-benzoic acid
methyl 4-[2-(1,1,4,4-tetramethyl-6-(3-methylbutyl)-1,2,3,4-tetrahydronaphth-7-yl)-vinyl]-benzoate
ethyl 4-[2-(1,1,4,4-tetramethyl-6-(3-methylbutyl)-1,2,3,4-tetrahydronaphth-7-yl)-vinyl]-benzoate
ethyl 4-[2-methyl-2-(1,1,3,3-tetramethyl-5-(3-methylbutyl)-indan-6-yl)-vinyl]-benzoate
ethyl 4-[2-methyl-2-(1,1,2,3,3-pentamethyl-5-(3-methylbutyl)-indan-6-yl)-vinyl]-benzoate
ethyl 4-[2-methyl-2-(1,1,4,4-tetramethyl-6-(3-methylbutyl)-1,2,3,4-tetrahydronaphth-7-yl)-vinyl]-benzoate
ethyl 4-[2-methyl-2-(1,1,4,4-tetramethyl-6-(3-ethylpentyl)-1,2,3,4-tetrahydronaphth-7-yl)-vinyl]-benzoate
methyl 4-[2-methyl-2-(1,1,3,3-tetramethyl-5-(3-ethylpentyl)-indan-6-yl)-vinyl]-benzoate
methyl 4-[2-methyl-2-(1,1,2,3,3-pentamethyl-5-(3-ethylpentyl)-indan-6-yl)-vinyl]-benzoate
methyl 4-[2-methyl-2-(1,1,3,3-tetramethyl-5-(3-methylpentyl)-indan-6-yl)-vinyl]-benzoate
methyl 4-[2-methyl-2-(1,1,2,3,3-pentamethyl-5-(3-methylpentyl)-indan-6-yl)-vinyl]-benzoate
methyl 4-[2-methyl-2-(1,1,4,4-tetramethyl-6-(3-methylpentyl)-indan-6-yl)-vinyl]-benzoate
In addition the following compounds should be mentioned:
4-[2-methyl-2-(1,1,4,4-tetramethyl-1,2,3,4-tetrahydronaphth-7-yl)-vinyl]-N-(tetrazol-5-yl)-benzamide, 4-[2-methyl-2-(1,1,4,4,6-pentamethyl-1,2,3,4-tetrahydronaphth-7-yl)-vinyl]-N-tetrazol-5-yl)-benzamide,
4-[2-methyl-2-(1,1,4,4-tetramethyl-6-ethyl-1,2,3,4-tetrahydronaphth-7-yl)-vinyl]-N-(tetrazol-5-yl)-benzamide,
4-[2-methyl-2-(1,1,4,4-tetramethyl-6-isopropyl-1,2,3,4-tetrahydronaphth-7-yl)-vinyl]-N-(tetrazol-5-yl)-benzamide,
4-[2-methyl-2-(1,1,2,3,3-pentamethylindan-6-yl)-vinyl]-N-(tetrazol-5-yl)-benzamide,
4-[2-methyl-2-(1,1,3,3-tetramethylindan-6-yl)-vinyl]-N-(tetrazol-5-yl)-benzamide,
4-[2-methyl-2-(1,1,4,4-tetramethyl-6-propyl-1,2,3,4-tetrahydronaphth-7-yl)-vinyl]-N-(tetrazol-5-yl)-benzamide,
4-[2-methyl-2-(1,1,4,4-tetramethyl-6-(2-methylpropyl)-1,2,3,4-tetrahydronaphth-7-yl)-vinyl]-N-(tetrazol-5-yl)-benzamide,
4-[2-methyl-2-(1,1,4,4-tetramethyl-6-butyl-1,2,3,4-tetrahydronaphth-7-yl)-vinyl]-N-tetrazol-5-yl)-benzamide,
4-[2-ethyl-2-(1,1,4,4-tetramethyl-1,2,3,4-tetrahydronaphth-7-yl)-vinyl]-N-(tetrazol-5-yl)-benzamide,
4-[2-ethyl-2-(1,1,4,4,6-pentamethyl-1,2,3,4-tetrahydronaphthyl-7-yl)-vinyl]-N-(tetrazol-5-yl)-benzamide,
4-[2-methyl-2-(1,1-dimethyl-1,2,3,4-tetrahydronaphth-7-yl)-vinyl]-N-(tetrazol-5-yl)-benzamide,
4-[2-methyl-1,1,6-trimethyl-1,2,3,4-tetrahydronaphth-7-yl)-vinyl]-N-(tetrazol-5-yl)-benzamide,
4-[2-methyl-2-(1,1,3,3,5-pentamethylindan-6-yl)-vinyl]-N-(tetrazol-5-yl)-benzamide,
4-[2-methyl-2-(1,1,2,3,3,5-hexamethylindan-6-yl)-vinyl]-N-(tetrazol-5-yl)-benzamide,
4-[2-methyl-2-(1,1,4,4-tetramethyl-1,2,3,4-tetrahydronaphth-7-yl)-vinyl]-benzoic acid 4-hydroxyanilide,
4-[2-methyl-2-(1,1,4,4,6-pentamethyl-1,2,3,4-tetrahydronaphth-7-yl)-vinyl]-benzoic acid 4-hydroxyanilide,
4-[2-methyl-2-(1,1,4,4-tetramethyl-6-ethyl-1,2,3,4-tetrahydronaphth-7-yl)-vinyl]-benzoic acid 4-hydroxyanilide,
4-[2-methyl-2-(1,1,4,4-tetramethyl-6-isopropyl-1,2,3,4-tetrahydronaphth-7-yl)-vinyl]-benzoic acid 4-hydroxyanilide,
4-[2-methyl-2-(1,1,2,3,3-pentamethylindan-6-yl)-vinyl]-benzoic acid 4-hydroxyanilide,
4-[2-methyl-2-(1,1,3,3-tetramethylindan-6-yl)-vinyl]-benzoic acid 4-hydroxyanilide,
4-[2-methyl-2-(1,1,4,4-tetramethyl-6-propyl-1,2,3,4-tetrahydronaphth-7-yl)-vinyl]-benzoic acid 4 hydroxyanilide,
4-[2-methyl-2-(1,1,4,4-tetramethyl-6-(2-methylpropyl)-1,2,3,4-tetrahydronaphth-7-yl)-vinyl]-benzoic acid 4 hydroxyanilide,
4-[2-methyl-2-(1,1,4,4-tetramethyl-6-butyl-1,2,3,4-tetrahydronaphth-7-yl)-vinyl]-benzoic acid 4-hydroxyanilide,
4-[2-ethyl-2-(1,1,4,4-tetramethyl-1,2,3,4-tetrahydronaphth-7-yl)-vinyl]-benzoic acid 4-hydroxyanilide,
4-[2-ethyl-2-(1,1,4,4,6-pentamethyl-1,2,3,4-tetrahydronaphth-7-yl)-vinyl]-benzoic acid 4-hydroxyanilide,
4-[2-methyl-2-(1,1-dimethyl-1,2,3,4-tetrahydronaphth-7-yl)-vinyl]-benzoic acid 4-hydroxyanilide,
4-[2-methyl-2-(1,1,6-trimethyl-1,2,3,4-tetrahydronaphth-7-yl)-vinyl]-benzoic acid 4-hydroxyanilide,
4-[2-methyl-2-(1,1,3,3,5-pentamethylindan-6-yl)-vinyl]-benzoic acid 4-hydroxyanilide and
4-[2-methyl-2-(1,1,2,3,3,5-hexamethylindan-6-yl)-vinyl]-benzoic acid 4-hydroxyanilide
4-[2-methyl-2-(1,1,3,3-tetramethyl-5-ethyl-indan-6-yl)-vinyl]-N-(tetrazol-5-yl)-benzamide
4-[2-methyl-2-(1,1,3,3-tetramethyl-5-propyl-indan-6-yl)-vinyl]-N-(tetrazol-5-yl)-benzamide
4-[2-methyl-2-(1,1,3,3-tetramethyl-5-butyl-indan-6-yl)-vinyl]-N-(tetrazol-5-yl)-benzamide
4-[2-methyl-2-(1,1,3,3-tetramethyl-5-pentyl-indan-6-yl)-vinyl]-N-(tetrazol-5-yl)-benzamide
4-[2-methyl-2-(1,1,3,3-tetramethyl-5-octyl-indan-6-yl)-vinyl]-N-(tetrazol-5-yl)-benzamide
4-[2-methyl-2-(1,1,2,3,3-pentamethyl-5-ethyl-indan-6-yl)-vinyl]-N-(tetrazol-5-yl)-benzamide
4-[2-methyl-2-(1,1,2,3,3-pentamethyl-5-propyl-indan-6-yl)-vinyl]-N-(tetrazol-5-yl)-benzamide
4-[2-methyl-2-(1,1,2,3,3-pentamethyl-5-butyl-indan-6-yl)-vinyl]-N-(tetrazol-5-yl)-benzamide
4-[2-methyl-2-(1,1,2,3,3-pentamethyl-5-pentyl-indan-6-yl)-vinyl]-N-(tetrazol-5-yl)-benzamide
4-[2-methyl-2-(1,1,2,3,3-pentamethyl-5-octyl-indan-6-yl)-vinyl]-N-(tetrazol-5-yl)-benzamide
4-[2-methyl-2-(1,1,2,3,3-pentamethyl-5-(2-methylpropyl)-indan-6-yl)-vinyl]-N-(tetrazol-5-yl)-benzamide
4-[2-methyl-2-(1,1,3,3-tetramethyl-5-(2-methylpropyl)-indan-6-yl)-vinyl]-N-(tetrazol-5-yl)-benzamide
4-[2-(1,1,2,3,3-pentamethyl-indan-6-yl)-vinyl]-N-(tetrazol-5-yl)-benzamide
4-[2-(1,1,2,3,3,5-hexamethyl-indan-6-yl)-vinyl]-N-(tetrazol-5-yl)-benzamide
4-[2-(1,1,3,3-tetramethyl-indan-6-yl)-vinyl]-N-(tetrazol-5-yl)-benzamide
4-[2-(1,1,3,3,5-pentamethyl-indan-6-yl)-vinyl]-N-(tetrazol-5-yl)-benzamide
4-[2-(1,1,4,4-tetramethyl-1,2,3,4-tetrahydronaphth-7-yl)-vinyl]-N-(tetrazol-5-yl)-benzamide
4-[2-(1,1,4,4,6-pentamethyl-1,2,3,4-tetrahydro-naphth-7-yl)-vinyl]-N-(tetrazol-5-yl)-benzamide
4-[2-methyl-2-(1,1,3,3-tetramethyl-5-ethyl-indan-6-yl)-vinyl]-benzoic acid 4-hydroxyanilide
4-[2-methyl-2-(1,1,3,3-tetramethyl-5-propyl-indan-6-yl)-vinyl]-benzoic acid 4-hydroxyanilide
4-[2-methyl-2-(1,1,3,3-tetramethyl-5-butyl-indan-6-yl)-vinyl]-benzoic acid 4-hydroxyanilide
4-[2-methyl-2-(1,1,3,3-tetramethyl-5-pentyl-indan-6-yl)-vinyl]-benzoic acid 4-hydroxyanilide
4-[2-methyl-2-(1,1,3,3-tetramethyl-5-octyl-indan-6-yl)-vinyl]-benzoic acid 4-hydroxyanilide
4-[2-methyl-2-(1,1,2,3,3-pentamethyl-5-ethyl-indan-6-yl)-vinyl]-benzoic acid 4-hydroxyanilide
4-[2-methyl-2-(1,1,2,3,3-pentamethyl-5-propyl-indan-6-yl)-vinyl]-benzoic acid 4-hydroxyanilide
4-[2-methyl-2-(1,1,2,3,3-pentamethyl-5-butyl-indan-6-yl)-vinyl]-benzoic acid 4-hydroxyanilide
4-[2-methyl-2-(1,1,2,3,3-pentamethyl-5-pentyl-indan-6-yl)-vinyl]-benzoic acid 4-hydroxyanilide
4-[2-methyl-2-(1,1,2,3,3-pentamethyl-5-octyl-indan-6-yl)-vinyl]-benzoic acid 4-hydroxyanilide
4-[2-methyl-2-(1,1,2,3,3-pentamethyl-5-(2-methylpropyl)-indan-6-yl)-vinyl]-benzoic acid 4-hydroxyanilide 4-[2-methyl-2-(1,1,3,3-tetramethyl-5-(2-methylpropyl)-indan-6-yl)-vinyl]-benzoic acid 4-hydroxyanilide 4-[2-(1,1,2,3,3-pentamethyl-indan-6-yl)-vinyl]-benzoic acid 4-hydroxyanilide 4-[2-(1,1,2,3,3,5-hexamethyl-indan-6-yl)-vinyl]-benzoic acid 4-hydroxyanilide 4-[2-(1,1,3,3-tetramethyl-indan-6-yl)-vinyl]-benzoic acid 4-hydroxyanilide 4-[2-(1,1,3,3,5-pentamethyl-indan-6-yl)-vinyl]-benzoic acid 4-hydroxyanilide 4-[2-(1,1,4,4-tetramethyl-1,2,3,4-tetrahydronaphth-7-yl)-vinyl]-benzoic acid 4-hydroxyanilide 4-[2-(1,1,4,4,6-pentamethyl-1,2,3,4-tetrahydronaphth-7-yl)-vinyl]-benzoic acid 4-hydroxyanilide.

The compounds according to the invention, where they are derivatives of the free benzoic acid, possess an acidic hydrogen atom, and can therefore be converted with a base, in a conventional manner, into a physiologically tolerated, readily water-soluble salt. Examples of suitable salts are ammonium salts, alkali metal salts, in particular those of sodium, potassium and lithium, alkaline earth metal salts, in particular those of calcium and magnesium, and salts with suitable organic bases, such as lower alkylamines, eg. methylamine or ethylamine, lower alkylamines which are substituted, in particular by hydroxyl, eg. diethanolamine, triethanolamine and tris(hydroxymethyl)-aminomethane, piperidine and morpholine.

If the novel compounds possess a tetrazole radical, their alkali metal and alkaline earth metal salts may be prepared.

The novel compounds are prepared by a process wherein (a) a compound of the formula II

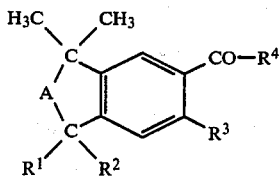

where A, $R^1$, $R^2$, $R^3$ and $R^4$ have the meanings given in claim 1, is subjected to a Wittig-Horner reaction with a phosphorus compound of the formula III

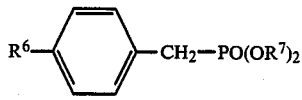

where $R^6$ has the meanings given for $R^5$ or is cyano, and $R^7$ is $C_1$–$C_4$-alkyl, or (b) a phosphonium salt of the formula IV

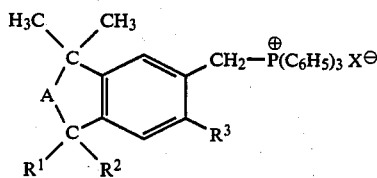

where A, $R^1$, $R^2$, $R^3$ and $R^4$ have the meanings given in claim 1 and X is chlorine or bromine, is subjected to a Wittig reaction with a benzaldehyde derivative of the formula

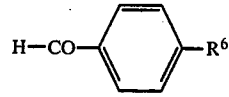

where $R^6$ has the above meanings, and thereafter, if R6 is not carboxyl, the resulting compound may, if desired, be hydrolyzed and the free acid, obtained either in this manner or directly, may, if desired, then be reacted with a $C_1$–$C_3$-alcohol, p-hydroxyaniline or 5-aminotetrazole, and the compound thus obtained may, if desired, be converted into its salt with physiologically tolerated bases.

The reactions (a) and (b) are carried out at not more than 100° C., advantageously at from 20° to 50° C., under atmospheric pressure, or under superatmospheric pressure in a closed vessel, the mixture being heated, if appropriate, to the stated temperature.

These reactions can be carried out in the presence of a diluent or solvent, for example a lower saturated dialkyl ether, dialkyl glycol ether or cyclic ether, eg. diethyl ether, ethyl tert.-butyl ether, 1,2-dimethoxyethane, tetrahydrofuran or dioxane, an aromatic hydrocarbon, eg. benzene, an alkylbenzene, eg. toluene or xylene, a saturated aliphatic hydrocarbon, eg. hexane, heptane or isooctane, a lower aliphatic ketone, eg. acetone, methyl ethyl ketone or methyl isobutyl ketone, or a dialkylformamide, eg. dimethylformamide or diethylformamide, or a mixture of the above solvents. A cyclic ether, eg. dioxane or tetrahydrofuran, or, in particular, dimethylformamide, or a mixture of these, is preferably employed, the reaction taking place in general at not more than 30° C.

The reaction is carried out in the presence of a deprotonating agent for the phosphorus compound (III). Suitable compounds of this type are alkali metal hydrides and alkali metal amides, in particular those of sodium and potassium, the sodium and potassium salts of dimethylsulfoxide, alkyl-lithium compounds, eg. n-butyl-lithium, and alkali metal alcoholates, preferably sodium methylate and sodium ethylate.

When an aliphatic epoxide compound, preferably butylene oxide, is used, it is possible to carry out the reaction without the addition of other agents. Aliphatic epoxide compounds are thus solvent and deprotonating agent at the same time. When butylene oxide is employed, the reaction can be carried out at the boiling point of the reaction mixture or at about 100° C., in a closed vessel, and at superatmospheric pressure.

To react an acid I, where $R^5$ is COOH, with a $C_1$–$C_3$-alcohol, p-hydroxyaniline or 5-aminotetrazole, the acid is converted into an activated derivative of the formula I where R is COX and X is a leaving group.

X is an acid radical, eg. halogen, in particular chlorine or bromine, or the N-hydroxysuccinimide radical.

The reaction is carried out at not more than 50° C. under atmospheric pressure, or under superatmospheric pressure in a closed vessel.

This reaction can be carried out in the presence of a diluent or solvent, for example a lower saturated dialkyl ether, dialkyl glycol ether or cyclic ether, such as diethyl ether, ethyl tert.-butyl ether, 1,2-dimethoxyethane, tetrahydrofuran or dioxane, an aromatic hydrocarbon, such as benzene, an alkylbenzene, such as toluene or xylene, a saturated aliphatic hydrocarbon, such as hexane, heptane or isooctane, a lower aliphatic ketone, such as acetone, methyl ethyl ketone or methyl isobutyl ketone, or a dialkylformamide, such as dimethylformamide or diethylformamide, or a mixture of the stated solvents. The linear or cyclic ether, eg. diethyl ether or tetrahydrofuran, or, in particular, dimethylformamide is preferably used, the reaction taking place in general at not more than 30° C.

The reaction is conventionally carried out in the presence of a base as the acid acceptor. Suitable bases are alkali metal carbonates and bicarbonates, in particular those of sodium and potassium, tertiary organic bases, eg. pyridine, and lower trialkylamines, eg. trimethylamine and triethylamine. The base is employed in a stoichiometric amount or in a slight excess, based on the benzoyl halide used.

In another possible method of preparing the novel acid derivatives, the corresponding free acid I, where $R^5$ is COOH, is used as a starting material, and is reacted with a $C_1$-$C_3$-alcohol, p-aminophenol or aminotetrazole, in a solvent, in the presence of a carboxyl-activating agent which eliminates water.

Suitable activating reagents which eliminate water are the reagents conventionally used in peptide synthesis (cf. The Peptides, Volume I, pages 77-128, Academic Press, New York, 1965). The general principle of the reaction comprises activation of the carboxyl group, for example by treatment with a carbodiimide, eg. N,N'-dicyclohexylcarbodiimide, or by intermediate formation of an acid azide, a mixed anhydride (for example with a monoester of carbonic acid), an activated ester (for example the p-nitrophenyl ester) or a heterocyclic amide (for example an imidazolide) of the corresponding benzoic acid.

A compound in which the carboxyl group has been activated may then be reacted with a $C_1$-$C_3$-alcohol, p-aminophenol or aminotetrazole to give the acid derivative according to the invention. The activation and linkage reactions can be carried out in a solvent, preferably in N,N-dimethylformamide, tetrahydrofuran, dioxane, methylene chloride, nitromethane, acetonitrile, dimethylsulfoxide, N,N-dimethylacetamide or hexamethylphosphorotriamide. The two stages, ie. the reaction of the acid with the coupling agent and the reaction of the activated intermediate with p-aminophenol may be carried out at from 20° to 100° C., either stepwise by isolating the activated intermediate before adding the p-aminophenol, or advantageously be carrying out the stages in succession, without isolation of intermediates.

In a preferred linkage method, the reaction is carried out using N,N-carbonyldiimidazole in dimethylformamide, the reaction temperature being from 20° to 60° C. for both stages.

The compounds of the formula I may be pure cis or trans isomers or mixtures of these. A mixture can be determined quantitatively by HPLC analysis or by a $^{13}$C-NMR spectrum, and the particular desired isomer can be isolated in pure form by fractional crystallization, chromatography with, for example, a silica gel column, or preparative HPLC.

The carbonyl compounds of the general formula II where $R^1$, $R^2$, $R^3$, $R^4$ and A have the meanings given above are prepared either by conventional processes or by carbonylation of the corresponding hydrocarbon of the general formula VI where $R^1$, $R^2$ and A have the meanings given for formula I. The compounds of formula VI are known from the literature or may be conveniently prepared by the route set out below involving conventional steps.

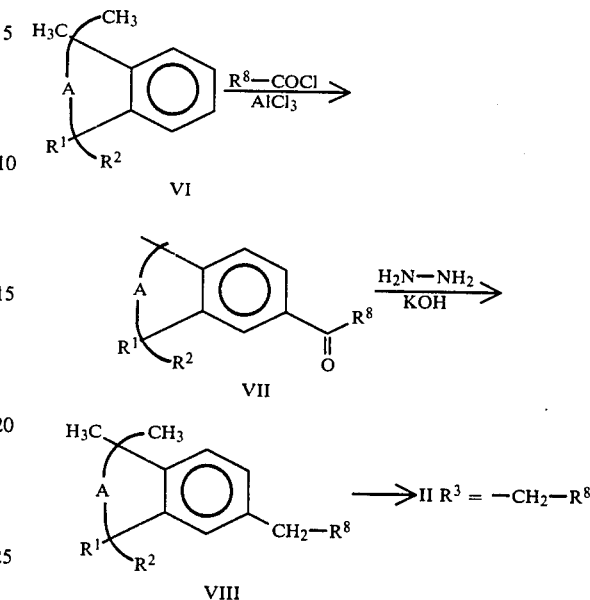

Compounds VII where $R^8$ is alkyl of 1 to 7 carbon atoms have been synthesized starting from hydrocarbons of the general formula VI under the conditions of a Friedel-Crafts reaction in the presence of a Lewis acid, particularly aluminum(III) chloride or iron(III) chloride. The carbonyl group in VII is preferably reduced under the conditions of a Wolff-Kishner reduction using hydrazine and potassium hydroxide in triethylene glycol, giving hydrocarbons of the formula VIII from which carbonyl compounds of the formula II may be synthesized by another Friedel-Crafts reaction.

To formylate VIII the usual reagents may be used, e.g. acid amides (Vilsmeier reaction), carbon monoxide and hydrogen chloride or hydrogen cyanide and hydrogen chloride.

The novel compounds and their physiologically tolerated salts can be used for the topical and systemic therapy and prophylaxis of benign and malignant neoplasms and premalignant lesions, eg. precancers and carcinomas of the skin, of the mucous membranes and of the internal organs, in the topical and systemic therapy of acne, psoriasis and other dermatological disorders accompanied by pathologically modified keratinization, and for the treatment of rheumatic disorders, in particular those of an inflammatory or degenerative nature, which affect the joints, muscles, tendons and other parts of the motive apparatus. A preferred field of indication, in addition to the therapy of dermatological disorders, is the prophylactic and therapeutic treatment of precancers and tumors. In this field, the low toxicity of the compounds is advantageous.

The pharmacological actions can be demonstrated, for example, in the following test models:

1. Elimination of keratinization in tracheal cultures as a demonstration of the antitumor action.

The test model is used to determine the intrinsic property of the novel compounds of increasing the differentiation of epithelial cells. The great significance of this screening method in predicting the potential use of a new retinoid for the prevention of tumors in epithelial tissue is generally recognized. Moreover, it is known that every in vitro test system has disadvantages in respect of the prediction of in vivo activity. Apart from these basic restrictions, tracheal cell cultures are one of the most useful methods of determining the biological activity of novel retinoids.

The ability of the test substances to eliminate keratinization in a defined in vitro system was determined. Tracheae of hamsters at a very early stage of vitamin A deficiency were used for culture. When the trachea was removed, the animals, which had been weaned at 21 days, were from 29 to 30 days old and still showed an increase in weight. Their average weight was from 47 to 52 g. The tracheal epithelium was in general slightly columnar or pavement-like and had only isolated areas of squamous metaplasia. Each trachea was opened along the membrane-like dorsal wall, from the larynx to the carina, and cultured in a serum-free medium (CMRL-1066 supplemented by 1.0 µg/ml of crystalline bovine insulin, 0.1 µg/ml of hydrocortisone hemisuccinate, 2mM of glutamine, 100 units/ml of penicillin and 100 µg/ml of streptomycin). The cultures were aerated with a mixture of 50% of oxygen, 45% of nitrogen and 5% of carbon dioxide, and the culture dishes were shaken gently to bring the tracheae into contact with the gas and the culture medium. All tracheae were initially kept for 3 days in the culture medium without the addition of retinoid. After this period, some tracheae were removed. Almost all of these exhibited substantial squamous metaplasia. The remaining tracheae were divided into groups, which were then treated with the following additives:

(a) The test substance dissolved in spectroscopically pure dimethylsulfoxide (the final concentration of dimethylsulfoxide in the culture medium was never greater than 0.1%).

(b) An equivalent amount of dimethylsulfoxide without a further additive.

The nutrient medium was changed three times per week. After culture for 10 days, the remaining tracheae were worked up by being fixed in 10% strength buffered formaldehyde solution and embedded in paraffin. 5 µm sections through the center were stained with hexatoxylin and eosin, and examined under the microscope to determine if keratin and keratohyalin were present; both were observed in about 90% of all control cultures kept in the absence of test substance. Dose-effect curves of the novel compounds were recorded. Table 1 below gives the extrapolated molar doses which suppress keratinization in half the cultures (ED 50%).

TABLE 1

| Substance of example | $ED_{50}$ [mole/liter] |
|---|---|
| 2 | $1.10^{-11}$ |
| 7 | $1.10^{-11}$ |
| 31 | $3.10^{-12}$ |
| 32 | $1.10^{-12}$ |
| 40 | $1.10^{-12}$ |
| Vitamin A acid | $1.10^{-11}$ |

Moreover, the compounds according to the invention (in particular the compound of Example 2) induce cell differentiation to give mature granulocytes in leukemia cells of patients having promyelocytic leukemia.

2. The antiarthritic action of the novel compounds can be determined in a conventional manner in an animal experiment based on the adjuvant arthritis model.

3. The dermatological activity, for example in the treatment of acne, can be demonstrated, inter alia, by means of the comedolytic acitivty.

The development of comedos was induced by one topical application of 0.5 ml per day, onto both ears of albino rabbits, of 5% of tar in Polyan ® (ester of lanolin alcohol and linolenic acid, produced by Amerchol Corp., U.S.A.), the application being carried out on 5 successive days per week over a period of two weeks. Thereafter, the test substances in ethanol/propylene glycol (70:30, v/v, 0.5 ml) were applied topically onto the inner skin area of one ear of each rabbit once per day on 5 successive days per week over a period of two weeks. The second ear of each animal served as an untreated control.

After further treatment for 72 hours with the test substance, the rabbits were sacrificed. A skin sample of about 6 cm² was taken from each auricle just outside the oratory passage, and this sample was divided into sections of about 1 cm². These pieces of skin were immersed for 2 minutes in warm water at 60° C. The epidermis was carefully peeled off using the flat end of a spatula and a small forceps, and was placed, dermal side up, on the slide. After drying in air overnight, the test strips were assessed under a stereomicroscope. Follicular pieces with keratose material remained intact. The comedos were recognizable as discrete, cylindrical to round keratose particles which were of similar appearance and whose size and number were proportional to the activity of the test substance. The comedolytic effect was determined as the decrease in the number of comedos, in %, compared with the control ear (cf. Table 2).

TABLE 2

| Substance of example | Concentration % | Comedolytic activity in % |
|---|---|---|
| Vitamin A acid | 0.1 | 67 |
| 1 | " | 75 |
| 2 | " | 73 |
| 5 | " | 54 |
| 6 | " | 68 |
| 7 | " | 59 |
| 8 | " | 62 |
| 10 | " | 31 |
| 11 | " | 40 |
| 14 | " | 79 |
| 15 | " | 59 |
| 17 | 0.2 | 56 |

4. Demonstration of the ability of the compounds to reduce the number of utriculi in the Rhino mouse model served as a further measure of the dermatological activity. In this method, which was described by L. H. Kligman et al in The Journal of Investigative Dermatology 73 (1979), 354–358, cysts which are present in Rhino mice as genetically caused skin lesions, ie. acne cysts, are caused to recede by administration of the active compound, and the decrease is expressed as a %.

TABLE 3

| Substance of example | concentration % | Decrease in % |
|---|---|---|
| Vitamin A acid | 0.1 | 60 |
| 1 | 0.1 | 65 |
| 2 | " | 68 |
| 5 | " | 69 |
| 6 | " | 59 |
| 7 | " | 62 |
| 8 | " | 52 |
| 10 | " | 49 |
| 11 | " | 59 |

TABLE 3-continued

| Substance of example | concentration % | Decrease in % |
| --- | --- | --- |
| 14 | " | 64 |
| 15 | " | 59 |
| 17 | 0.2 | 62 |
| 18 | 0.2 | 42 |
| 19 | 0.1 | 12 |
| 20 | 0.1 | 6 |
| 23 | 0.2 | 62 |
| 24 | 0.2 | 42 |
| 25 | 0.2 | 60 |

5. The toleration of the test substances after topical administration was determined in experiments with 6 white male New Zealand rabbits in each case. In the case of each test animal, an area of about 6 cm² on the back was shaved. The test substances were dissolved in ethanol/propylene glycol (70:30, v/v), and 0.2 ml of this solution was applied with an automatic micropipette on 9 successive days by carefully rubbing the solution into a particular point twice daily at 6-hour intervals.

Before each application in the morning, all test areas were assessed subjectively in respect of erythemas and scaling, a numerical scale from 0 to 3 being employed (0=no reaction, 1=mild, 2=moderate and 3=severe). The average erythema formation and scaling gives the relative irritant level of the test substances in comparison with vitamin A acid.

TABLE 4

| Substance of example | Erythema | Scaling |
| --- | --- | --- |
| 2 | 2.8 | 2.7 |
| 5 | 2.0 | 1.7 |
| 7 | 3.0 | 3.0 |
| 8 | 1.4 | 1.0 |
| Vitamin A acid | 3.0 | 3.0 |

Accordingly, the present invention also relates to the therapeutic agents for topical and systemic use which in addition to conventional carriers or diluents contain a compound of the formula (I) as the active compound, and to the use of a compound of the formula (I) for the preparation of a drug.

The therapeutic agents or formulations are prepared using the conventional liquid or solid carriers or diluents and the conventional pharmaceutical auxiliaries, in accordance with the desired route of administration and using a dose suitable for use, the preparation being carried out in a conventional manner, for example by mixing the active compound with the solid or liquid carrier or auxiliary conventionally used in such formulations.

The drugs can accordingly be administered perorally, parenterally or topically. Examples of formulations of this type are tablets, film tablets, coated tablets, capsules, pills, powders, solutions, suspensions, infusion solutions, injection solutions, pastes, ointments, gels, creams, lotions, powders, solutions, emulsions and sprays.

The therapeutic agents can contain the novel compounds in a concentration of from 0.001 to 1%, preferably from 0.001 to 0.01%, when used locally, and preferably as an individual dose of from 0.1 to 50 mg when used systemically, and may be administered daily in one or more doses, depending on the nature and severity of the disorder.

Examples of conventionally used pharmaceutical auxiliaries are alcohols, eg. isopropanol, oxyethylated castor oil or oxyethylated hydrogenated castor oil, polyacrylic acid, glycerol monostearate, paraffin oil, vaseline, wool fat, polyethylene glycol 400, polyethylene glycol 400 stearate and oxyethylated fatty alcohols for local administration, and lactose, propylene glycol and ethanol, starch, talc and polyvinylpyrrolidone for systemic administration. The formulations may or may not contain antioxidants, eg. tocopherol, or butylated hydroxyanisole or butylated hydroxytoluene, flavor-improving additives, stabilizers, emulsifiers, lubricants, etc. All substances used in the preparation of the pharmaceutical formulation should be toxicologically acceptable, and tolerated by the active compounds used.

The examples which follow illustrate the preparation of the compounds according to the invention.

Production of the starting compounds

EXAMPLE A 1,1,2,3,3-pentamethyl-5-indanyl-isopropylketone

A solution of 190 g of 1,1,2,3,3-pentamethylindan and 240 ml of trichloroethylene was dripped in the course of 2 hours into a suspension, at approx. 3° C., of 154 g of 2-methylpropionyl chloride, 220 ml of trichloroethylene and 151 g of anhydrous aluminum chloride and the mixture stirred overnight at icebath temperature. The entire reaction mixture was then poured into 2.5 l of ice water and extracted with methylene chloride. The organic extracts were dried over sodium sulfate. The solvents were distilled off and the evaporation residue distilled. 206 g of 1,1,2,3,3-pentamethyl-5-indanylisopropylketone, b.p. 114°–120° C. (0.1 mbar), $n_D^{21}$ 1.5214, were obtained. The $^1H$ NMR spectrum (in $CDCl_3^3$) corresponded to the structure.

EXAMPLE B 1,1,2,3,3-pentamethyl-5-(2-methylpropyl)-indan 176 g of 1,1,2,3,3-pentamethyl-5-indanyl-isopropylketone, 102 g of hydrazine hydrate, 152 g of potassium hydroxide and 350 ml of triethylene glycol were heated slowly to 200° C. while stirring, the water of reaction being distilled off through a short Vigreux column. Stirring was then continued for 6 hours at approx. 200° C. The reaction mixture was allowed to cool to approx. 80° C., mixed with 500 ml of water and the mixture extracted several times with diethyl ether. The combined organic extracts were dried over sodium sulfate and freed from solvent. The evaporation residue was distilled. 134 g of 1,1,2,3,3-pentamethyl-5-(2-methylpropyl)-indan b.p. 85°–90° C. (0.1 mbar), $n_D^{22}$ 1.5022, were obtained. The $^1H$ NMR spectrum (in $CDCl_3^3$) corresponded to the structure.

EXAMPLE C 1,1,2,3,3-pentamethyl-6-(2-methylpropyl)-5-indanylmethylketone

A solution of 133 g of 1,1,2,3,3-pentamethyl-5-(2-methylpropyl)inan and 170 ml of trichloroethylene was dripped in the course of an hour into a suspension, at approx. 3° C., of 48 g of acetyl chloride, 120 ml of trichloroethylene and 82 g of anhydrous aluminum chloride. Stirring was continued for 5 hours at icebath temperature and the reaction mixture poured into 1 l of ice water and extracted with methylene chloride. The organic extracts were dried over sodium sulfate. The solvents were distilled off and the evaporation residue distilled.

137 g of 1,1,2,3,3-pentamethyl-6-(2-methylpropyl)-5-indanyl-methylketone, b.p. 110°–112° C. (0.15 mbar), $n_D^{22}$ 1.5114, was obtained. The $^1$H NMR spectrum (in $CDCl_3^3$) corresponded to the structure.

Production of the final compounds

EXAMPLE 1

Ethyl E-4-[2-methyl-2-(1,1,4,4,6-pentamethyl-1,2,3,4-tetrahydronaphth-7-yl)-vinyl]-benzoate A solution of 90 g of diethyl p-carboxyethylbenzylphosphonate in 150 ml of dimethylsulfoxide was added dropwise, in the course of 0.5 hour, at 35° C., to a suspension of 9 g of 80% strength sodium hydride, which had beforehand been freed from the 20% of paraffin with petroleum ether, in 250 ml of dimethylsulfoxide. Thereafter, the mixture was stirred for a further 2 hours at 40° C., and a solution of 36.6 g of 7-acetyl-1,1,4,4,6-pentamethyltetralin in 70 ml of dimethylsulfoxide was added dropwise in the course of 10 minutes.

The mixture was allowed to stand overnight, after which 100 ml of ethanol were added, and the mixture was poured onto 2 liters of ice/water and acidified with 2N hydrochloric acid. The resulting precipitate was filtered off, and washed on the filter with 150 ml of ethanol and with 75 ml of methanol. 35 g of ethyl E-4-[2-methyl-2-(1,2,4,4,6-pentamethyl-1,2,3,4-tetrahydronaphth-7-yl)-vinyl]-benzoate of melting point 108°–109° C. remained.

HPLC analysis (Si 60 5 μm, 150 bar, 98:2 n-heptane/ethyl acetate, $t_R = 3.1$ min) showed that the product contained more than 98% of one isomer.

$^{13}$C-NMR spectrum ($CDCl_3$, data in ppm): (The carbon atoms were numbered arbitrarily in order to assign the NMR signals)

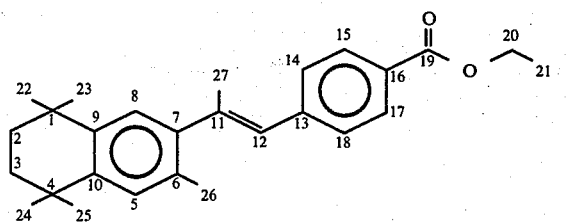

14.40 ($C_{21}$); 19.74 ($C_{27}$); 20.35 ($C_{26}$); 31.96 ($C_{25}$, $C_{24}$, $C_{23}$, $C_{22}$); 34.02 ($C_1$, $C_4$); 35.32 ($C_2$, $C_3$); 60.94 ($C_{20}$); 126.11 ($C_8$); 128.41 ($C_{16}$, $C_{12}$); 128.55 ($C_5$); 129.00 ($C_{14}$, $C_{18}$); 129.68 ($C_{15}$, $C_{17}$); 131.72 ($C_6$); 141.98 ($C_{13}$); 142.93 ($C_{11}$); 143.11 ($C_{10}$); 143.83 ($C_9$); 166.80 ($C_{19}$).

The signal at 19.74 ($C_{27}$) confirms the E (trans) geometry of the compound.

EXAMPLE 2

4.7 g of ethyl E-4-[2-methyl-2-(1,1,4,4,6-pentamethyl-1,2,3,4-tetrahydronaphth-7-yl)-vinyl]-benzoate was stirred with 1.7 g of 86% strength potassium hydroxide in a mixture of 100 ml of ethanol and 5 ml of water for 6 hours at 80° C. The total reaction mass was introduced into 1 liter of water, the mixture was acidified with 2N hydrochloric acid, and the colorless precipitate obtained was filtered off, dried and then washed on a suction filter with 100 ml of heptane. After drying, 4.0 g of E-4-[2-methyl-2-(1,1,4,4,6-pentamethyl-1,2,3,4-tetrahydronaphth-7-yl)-vinyl]-benzoic acid of melting point 206° C. remained.

$^{13}$C-NMR spectrum ($d_6$-dimethylsulfoxide, data in ppm): (The carbon atoms were numbered arbitrarily in order to assign the NMR signals).

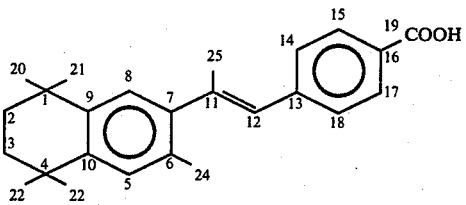

19.36 ($C_{25}$); 20.17 ($C_{24}$); 31.60 ($C_{20}$, $C_{21}$, $C_{22}$, $C_{23}$); 33.51 ($C_2$, $C_3$); 34.71 ($C_4$, $C_1$); 125.40 ($C_8$); 128.00 ($C_5$, $C_{12}$); 128.61 ($C_{16}$); 128.95; 129.42 ($C_{14}$, $C_{18}$); 129.42 ($C_{15}$, $C_{17}$); 131.12 ($C_6$); 141.20 ($C_{13}$); 141.70 ($C_7$); 142.16 ($C_{10}$); 142.52 ($C_{11}$); 143.08 ($C_9$); 167.26 ($C_{19}$).

The signal at 19.36 ($C_{25}$) confirms the E (trans) geometry of the compound.

EXAMPLE 3

A. Preparation of the starting material 9 g of 80% strength sodium hydride which had beforehand been freed from the 20% of paraffin with petroleum ether was suspended in 100 ml of dimethylsulfoxide, and a solution of 75.9 g of diethyl p-cyanobenzylphosphonate in 150 ml of dimethylsulfoxide was added dropwise in the course of 0.5 hour, at about 35° C. The mixture was stirred for a further 2 hours at 40° C., and a solution of 53.5 g of 7-acetyl-1,1,4,4,6-pentamethyltetralin in 50 ml of dimethylsulfoxide was added dropwise in the course of 10 minutes.

On the next day, the reaction mixture was poured onto 3 liters of ice/water, and acidified with 2N hydrochloric acid. The resulting solid was filtered off, and washed on the filter with 75 ml of methanol. After drying, 30.2 g of E-4-[2-methyl-2-(1,1,4,4,6-pentaethyl-1,2,3,4-tetrahydronaphth-7-yl)-vinyl]-benzonitrile of melting point 140°–141° C. remained.

HPLC analysis (Si 60 5 μm, 150 bar, 25 cm column, 97:3 n-heptane/ethyl acetate, $t_R = 3.2$ min) showed that the product contained more than 95% of one isomer.

B. Preparation of the end product 13.5 g of E-4-[2-methyl-2-(1,1,4,4,6-pentamethyl-1,2,3,4-tetrahydronaphth-7-yl)-vinyl]-benzonitrile in a mixture of 200 ml of ethanol and 200 ml of 10N sodium hydroxide solution were heated at the boil for 3 hours. The mixture was then cooled, after which it was poured onto 1 liter of water, and the colorless precipitate was filtered off under suction and dried to give 14.9 g of E-4-[2-methyl-2-(1,1,4,4,6-pentamethyl-1,2,3,4-tetrahydronaphth-7-yl)-vinyl]-benzoic acid of melting point 204°–206° C. (cf. Example 2).

The compounds given in the table below were prepared either by a Wittig-Horner reaction or by hydrolysis of the corresponding ester or nitrile.

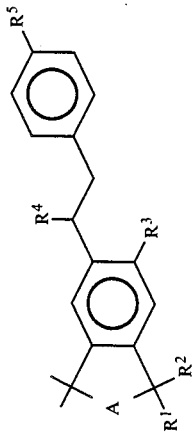

| No. | A | $R^1$ | $R^2$ | $R^3$ | $R^4$ | $R^5$ | Mp [°C.] | Stereo-chemistry | Chemical shift ($^{13}C$—NMR) of $R^4$ [ppm] | Name |
|---|---|---|---|---|---|---|---|---|---|---|
| 4 | —CH$_2$CH$_2$— | —CH$_3$ | —CH$_3$ | —C$_2$H$_5$ | —CH$_3$ | —COOC$_2$H$_5$ | 100–102 | E | 20.96 | Ethyl E—4-[2-methyl-2-(1,1,4,4-tetramethyl-6-ethyl-1,2,3,4-tetrahydronaphth-7-yl)-vinyl]-benzoate |
| 5 | —CH$_2$—CH$_2$— | —CH$_3$ | —CH$_3$ | —C$_2$H$_5$ | —CH$_3$ | —COOH | 177–178 | E | 20.77 | E—4-[2-methyl-2-(1,1,4,4-tetramethyl-6-ethyl-1,2,3,4-tetrahydronaphth-7-yl)-vinyl]-benzoic acid |
| 6 | —CH$_2$—CH$_2$— | —CH$_3$ | —CH$_3$ | —CH(CH$_3$)$_2$ | —CH$_3$ | —COOC$_2$H$_5$ | 156–157 | E | 21.43 | Ethyl E—4-[2-methyl-2-(1,1,4,4-tetramethyl-6-isopropyl-1,2,3,4-tetrahydronaphth-7-yl)-vinyl]-benzoate |
| 7 | —CH$_2$—CH$_2$— | —CH$_3$ | —CH$_3$ | —CH(CH$_3$)$_2$ | —CH$_3$ | —COOH | 237–238 | E | 21.22 | E—4-[2-methyl-2-(1,1,4,4-tetramethyl-6-isopropyl-1,2,3,4-tetrahydronaphth-7-yl)-vinyl]benzoic acid |
| 8 | —CH$_2$—CH$_2$— | —CH$_3$ | —CH$_3$ | —CH$_2$—CH(CH$_3$)(CH$_3$) | —CH$_3$ | —COOH | 228–229 | E | 21.03 | E—4-[2-methyl-2-(1,1,4,4-tetramethyl-6-(2-methylpropyl)-1,2,3,4-tetrahydronaphth-7-yl)-vinyl]-benzoic acid |
| 9 | —CH$_2$—CH(CH$_3$)— | —CH$_3$ | —CH$_3$ | —CH$_3$ | —CH$_3$ | —COOC$_2$H$_5$ | 105 | E | 20.05 | Ethyl E—4-[2-methyl-2-(1,1,3,4,4,6-hexamethyl-1,2,3,4-tetrahydronaphth-7-yl)-vinyl]-benzoate |
| 10 | —CH$_2$—CH$_2$— | —CH$_3$ | —CH$_3$ | —CH$_3$ | —CH$_3$ | —COOH | 276–277 | Z | 27.1 | Z—4-[2-methyl-2-(1,1,4,4,6-pentamethyl-1,2,3,4-tetrahydronaphth-7-yl)-vinyl]-benzoic acid |
| 11 | —CH$_2$—CH$_2$— | —CH$_3$ | —CH$_3$ | —CH$_2$—CH$_2$—CH$_3$ | —CH$_3$ | —COOH | 198–199 | E | 22.04 | E—4-[2-methyl-2-(1,1,4,4-tetramethyl-6-propyl-1,2,3,4-tetrahydronaphth-7-yl)-vinyl]-benzoic acid |
| 12 | —CH$_2$—CH(CH$_3$)— | —CH$_3$ | —CH$_3$ | —CH$_3$ | —CH$_3$ | —COOH | 254 | E | 20.11 | E—4-[2-methyl-2-(1,1,3,4,4,6-hexamethyl-1,2,3,4-tetrahydronaphth-7-yl)-vinyl]-benzoic acid |
| 13 | —CH$_2$—CH$_2$— | —CH$_3$ | —CH$_3$ | —CH$_3$ | —CH$_2$—CH$_3$ | —COOH | 252 | Z | 32.79 (—CH$_2$—) | E—4-[2-ethyl-2-(1,1,4,4-tetramethyl-1,2,3,4-tetrahydronaphth-7-yl)-vinyl]-benzoic acid |

-continued

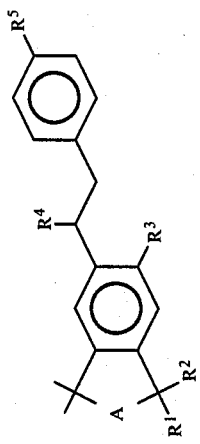

| No. | A | R¹ | R² | R³ | R⁴ | R⁵ | Mp [°C] | Stereo-chemistry | Chemical shift ($^{13}$C—NMR) of R⁴ [ppm] | Name |
|---|---|---|---|---|---|---|---|---|---|---|
| 14 | —CH₂—CH₂— | CH₃ | CH₃ | n-Bn | CH₃ | COOH | 237-240 | E | | E—4-[2-methyl-2-(1,1,4,4-tetramethyl-6-n-butyl-1,2,3,4-tetrahydronaphth-7-yl)-vinyl]-benzoic acid |
| 15 | —CH₂—CH₂— | CH₃ | CH₃ | n-Oct | CH₃ | COOH | 130-131 | E | 20.83 | E—4-[2-methyl-2-(1,1,4,4-tetramethyl-6-n-octyl-1,2,3,4-tetrahydronaphth-7-yl)-vinyl]-benzoic acid |
| 16 | —CH₂—CH₂— | H | H | CH₃ | CH₃ | COOH | 233-234 | Z | 27.30 | Z—4-[2-methyl-2-(1,1-dimethyl-6-methyl-1,2,3,4-tetrahydronaphth-7-yl)-vinyl]-benzoic acid |
| 17 | —CH₂—CH₂— | —CH₃ | —CH₃ | —CH₂CH(CH₃)CH₃ | —CH₃ | —COOH | 273-274 | Z | 27.88 | Z—4-[2-methyl-2-(1,1,4,4-tetramethyl-6-(2-methylpropyl)-1,2,3,4-tetrahydronaphth-7-yl)-vinyl]-benzoic acid |
| 18 | H₃—C—CH | —CH₃ | —CH₃ | —CH₂CH(CH₃)CH₃ | —CH₃ | —COOH | 228-229 | E | 21.05 | E—4-[2-methyl-2-(1,1,2,3,3-pentamethyl-5-(2-methylpropyl)-indan-6-yl)-vinyl]-benzoic acid |
| 19 | —CH₂—CH₂— | —CH₃ | —CH₃ | —CH₂CH(CH₃)CH₃ | CH₃ | —COOC₂H₅ | 101-102 | E | 20.98 | ethyl E—4-[2-methyl-2-(1,1,4,4-tetramethyl-6-(2-methylpropyl)-1,2,3,4-tetrahydronaphth-7-yl)-vinyl]-benzoate |
| 20 | —CH₂—CH₂— | —CH₃ | —CH₃ | —CH₂CH(CH₃)CH₃ | CH₃ | —COOCH₃ | 228-229 | E | 20.99 | methyl E—4-[2-methyl-2-(1,4,4-tetramethyl-6-(2-methylpropyl)-1,2,3,4-tetrahydronaphth-7-yl)-vinyl]-benzoate |
| 21 | —CH₂—CH₂— | —CH₃ | —CH₃ | —CH₂CH(CH₃)CH₃ | CH₃ | —COOC₃H₇ | 68-69 | E | 21.28 | propyl E—4-[2-methyl-2-(1,1,4,4-tetramethyl-6-(2-methylpropyl)-1,2,3,4-tetrahydronaphth-7-yl)-vinyl]-benzoate |

-continued

| No. | A | R¹ | R² | R³ | R⁴ | R⁵ | Mp [°C] | Stereo-chemistry | Chemical shift ($^{13}C$—NMR) of R⁴ [ppm] | Name |
|---|---|---|---|---|---|---|---|---|---|---|
| 22 | —CH₂— | —CH₃ | —CH₃ | —CH₂CH(CH₃)CH₃ | CH₃ | —COOH | 216-217 | E | 21.05 | E—4-[2-methyl-2-(1,1,3,3-tetramethyl-5-(2-methylpropyl)-indan-6-yl)-vinyl]-benzoic acid |
| 23 | —CH₂—CH₂— | —CH₃ | —CH₃ | —CH₂—CH₂CH(CH₃)CH₃ | —CH₃ | —COOH | 174-175 | E | 20.86 | E—4-[2-methyl-2-(1,1,4,4-tetramethyl-6-(3-methylbutyl)-1,2,3,4-tetrahydronaphth-7-yl)-vinyl]-benzoic acid |
| 24 | H₃C—CH | —CH₃ | —CH₃ | nC₈H₁₇ | —CH₃ | —COOH | 137-138 | Z | 20.97 | E—4-[2-methyl-2-(1,1,2,3,3-pentamethyl-5-n-octyl-indan-6-yl)-vinyl]-benzoic acid |
| 25 | H₃C—CH | —CH₃ | —CH₃ | —CH₂—CH₂—CH(CH₃)CH₃ | —CH₃ | —COOH | 179-180 | E | 20.98 | E—4-[2-methyl-2-(1,1,2,3,3-pentamethyl-5-(3-methylbutyl)-indan-6-yl)-vinyl]-benzoic acid |
| 26 | —CH₂—CH₂ | —CH₃ | —CH₃ | —nC₄H₉ | —CH₃ | —COOH | 184-185 | Z | 27.92 | E—4-[2-methyl-2-(1,1,4,4-tetramethyl-6-n-butyl-1,2,3,4-tetrahydronaphth-7-yl)-vinyl]-benzoic acid |
| 27 | H₃C—CH | —CH₃ | —CH₃ | —C₂H₅ | —CH₃ | —COOH | 210-211 | E | 21.16 | E—4-[2-methyl-2-(1,1,2,3,3-pentamethyl-5-ethylindan-6-yl)-vinyl]-benzoic acid |
| 28 | H₃C—CH | —CH₃ | —CH₃ | —CH₃ | —CH₃ | —COOH | 212-213 | E | 20.96 | E—4-[2-methyl-2-(1,1,2,3,3-pentamethyl-5-propyl-indan-6-yl)-vinyl]-benzoic acid |
| 29 | H₃C—CH | —CH₃ | —CH₃ | —C₄H₉ | —CH₃ | —COOH | 179-180 | E | 20.97 | E—4-[2-methyl-2-(1,1,2,3,3-pentamethyl-5-butyl-indan-6-yl)-vinyl]-benzoic acid |

EXAMPLE 30

Gaseous hydrogen chloride was passed into a solution of 4.0 g of E-4-[2-methyl-2-(1,1,4,4,6-pentamethyl-1,2,3,4-tetrahydronaphth-7-yl)-vinyl]-benzoic acid in 300 ml of ethanol at the boiling point of the reaction mixture, until the solution was saturated. Thereafter, the mixture was kept at the boil for a further 4 hours, cooled, flushed with nitrogen and then evaporated down. The residue was digested with 30 ml of methanol, and the product was filtered off and dried. 3.6 g of ethyl E-4-[2-methyl-2-(1,1,4,4,6-pentamethyl-1,2,3,4-tetrahydronaphth-7-yl)-vinyl]-benzoate of melting point 109°–110° C. were obtained (cf. Example 1).

EXAMPLE 31

A solution of 5.3 ml of thionyl chloride in 10 ml of tetrahydrofuran was added rapidly to a suspension of 20.9 g of E-4-[2-methyl-2-(1,1,4,4-tetramethyl-1,2,3,4-tetrahydronaphth-7-yl)-vinyl]-benzoic acid (cf. Example 2) and 5.8 ml of pyridine in 200 ml of anhydrous tetrahydrofuran, and the mixture was stirred for two hours at room temperature. Thereafter, the precipitate formed was filtered off and the filtrate was made up with tetrahydrofuran to a total volume of 240 ml.

100 ml of this solution was added a little at a time, in the course of 10 minutes, to a suspension of 8.2 g of p-aminophenol in 100 ml of tetrahydrofuran, and stirring was then continued for a further 20 hours at room temperature. The reaction mixture was stirred into 1 liter of water, the mixture was acidified with 2N hydrochloric acid, and the resulting precipitate was filtered off, and recrystallized from ethanol with the addition of water. The product was filtered off and dried, and 11.1 g of E-4-[2-methyl-2-(1,1,4,4-tetramethyl-1,2,3,4-tetrahydronaphth-7-yl)-vinyl]-benzoic acid 4-hydroxyanilide of melting point 252°–253° C. remained. $^{13}$C-NMR spectrum (d$_6$-dimethylsulfoxide)

The resonance signal which appears at 17.30 ppm and may be assigned to the methyl group on carbon atom 2 of the olefinic ethylene group indicates that the compound obtained is the E (trans) isomer.

EXAMPLES 32 TO 37

The compounds listed in the table below were obtained by a procedure similar to that described in Example 18:

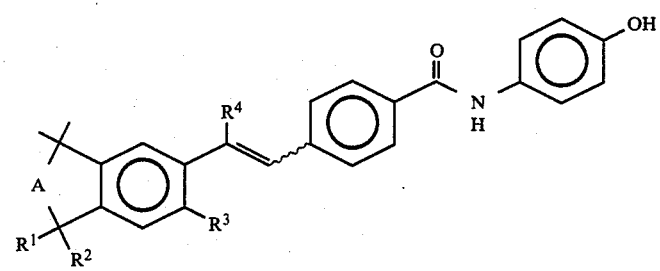

| No. | A | $R^1$ | $R^2$ | $R^3$ | $R^4$ | Mp [°C.] | Stereochemistry | Chemical shift ($^{13}$C—NMR) of $R^4$ [ppm] | Name |
|---|---|---|---|---|---|---|---|---|---|
| 32 | H$_3$C—CH$\diagup$$\diagdown$ | —CH$_3$ | —CH$_3$ | H | —CH$_3$ | 233–234 | E | 17.57 | E-4-[2-methyl-2-(1,1,2,3,3-pentamethylindan-6-yl)-vinyl]-benzoic acid 4-hydroxyanilide |
| 33 | —CH$_2$—CH$_2$— | —CH$_3$ | —CH$_3$ | —CH$_3$ | —CH$_3$ | 271–272 | E | 20.15 | E-4-[2-methyl-2-(1,1,4,4,6-pentamethyl-1,2,3,4-tetrahydronaphth-7-yl)-vinyl]-benzoic acid 4-hydroxyanilide |
| 34 | —CH$_2$—CH$_2$— | —CH$_3$ | —CH$_3$ | —CH$_2$—CH$_3$ | —CH$_3$ | 233–234 | E | 21.00 | E-4-[2-methyl-(1,1,4,4-tetramethyl-6-ethyl-1,2,3,4-tetrahydronaphth-7-yl)-vinyl]-benzoic acid 4-hydroxyanilide |
| 35 | —CH$_2$—CH$_2$— | —CH$_3$ | —CH$_3$ | —CH$\diagup$CH$_3$$\diagdown$CH$_3$ | —CH$_3$ | 229–230 | E | 21.19 | E-4-[2-methyl-2-(1,1,4,4-tetramethyl-6-isopropyl-1,2,3,4-tetrahydronaphth-7-yl)-vinyl]-benzoic acid 4-hydroxyanilide |
| 36 | —CH$_2$— | —CH$_3$ | —CH$_3$ | H | —CH$_3$ | >300 | E | 17.56 | E-4-[2-methyl-(1,1,3,3-tetramethylindan-6-yl)-vinyl]-benzoic acid 4-hydroxyanilide |

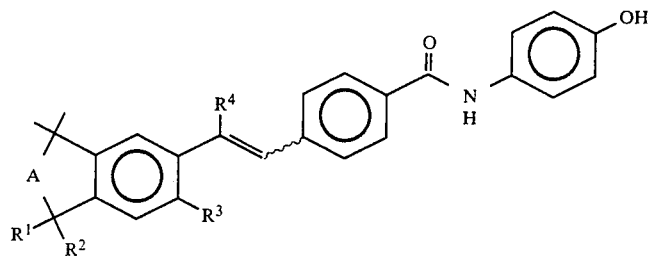

| No. | A | R¹ | R² | R³ | R⁴ | Mp [°C.] | Stereo-chemistry | Chemical shift ($^{13}C$—NMR) of R⁴ [ppm] | Name |
|---|---|---|---|---|---|---|---|---|---|
| 37 | —CH₂—CH₂— | —CH₃ | CH₃ | —CH₂—CH(CH₃)CH₃ | CH₃ | 203 | E | | E-4-[2-methyl-(1,1,4,4-tetra-methyl-6-(2-methylpropyl-1,2,3,4-tetrahydronaphth-7-yl)-vinyl]-benzoic acid 4-hydroxyanilide |

EXAMPLE 38

A solution of 0.5 ml of thionyl chloride in 5 ml of tetrahydrofuran was added rapidly to a suspension of 1.8 g of E-4-[2-methyl-2-(1,1,4,4-tetramethyl-1,2,3,4-tetrahydronaphth-7-yl)-vinyl]-benzoic acid (cf. Example 2) and 0.5 ml of pyridine in 15 ml of tetrahydrofuran, and the mixture was stirred for 2 hours at room temperature. Thereafter, the precipitate formed was filtered off, the filtrate was added to a suspension of 0.5 g of anhydrous 5-aminotetrazole and 0.5 g of pyridine in 20 ml of tetrahydrofuran, and the mixture was then stirred for a further 20 hours at room temperature. The reaction mass was stirred into 400 ml of water and acidified with 2N hydrochloric acid, and the resulting precipitate was filtered off and washed with methanol and petroleum ether. 1.7 g of E-4-[2-methyl-2-(1,1,4,4-tetramethyl-1,2,3,4-tetrahydronaphth-7-yl)-vinyl]-N-(tetrazol-5-yl)-benzamide of melting point 289°–290° C. remained.

C-NMR spectrum (d₆-dimethylsulfoxide)

The resonance signal which appeared at 17.41 ppm and may be assigned to the methyl group on carbon atom 2 of the olefinic ethylene group indicated that the compound obtained was the E (trans) isomer.

EXAMPLES 39 TO 44

The compounds listed in the table below were obtained by a procedure similar to that described in Example 1:

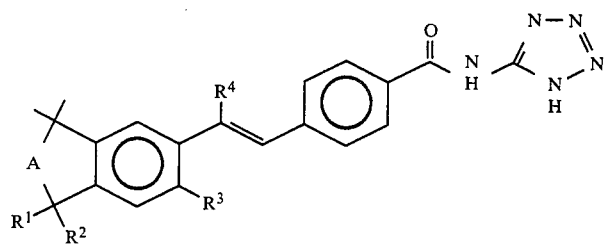

| No. | A | R¹ | R² | R³ | R⁴ | Mp [°C.] | Stereo-chemistry | Chemical shift ($^{13}C$—NMR) of R⁴ [ppm] | Name |
|---|---|---|---|---|---|---|---|---|---|
| 39 | —CH₂—CH₂— | —CH₃ | —CH₃ | —CH₃ | —CH₃ | 287–288 | E | 20.17 | E-4-[2-methyl-2-(1,1,4,4,6-pentamethyl-1,2,3,4-tetrahydronaphth-7-yl)-vinyl]-N—(tetrazol-5-yl)-benzamide |
| 40 | H₃C—CH< | —CH₃ | —CH₃ | H | —CH₃ | 285–286 | E | 17.76 | E-4-[2-methyl-2-(1,1,2,3,3,-pentamethylindan-6-yl)-vinyl]-N—(tetrazol-5-yl)-benzamide |
| 41 | —CH₂—CH₂— | —CH₃ | —CH₃ | —CH₂—CH₃ | —CH₃ | 280–281 | E | 20.81 | E-4-[2-methyl-(1,1,4,4-tetramethyl-6-ethyl-1,2,3,4-tetrahydronaphth-7-yl)-vinyl]-N—tetrazol-5-yl)-benzamide |

-continued

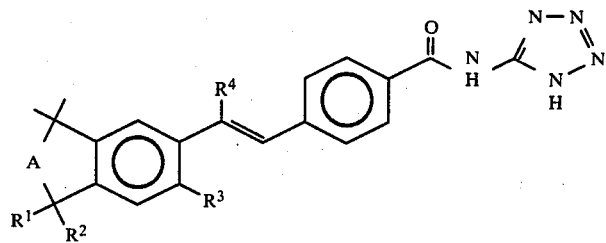

| No. | A | $R^1$ | $R^2$ | $R^3$ | $R^4$ | Mp [°C.] | Stereo-chemistry | Chemical shift ($^{13}C$—NMR) of $R^4$ [ppm] | Name |
|---|---|---|---|---|---|---|---|---|---|
| 42 | —$CH_2$—$CH_2$— | —$CH_3$ | —$CH_3$ | —CH(CH$_3$)$_2$ | —$CH_3$ | 296–297 | E | 21.26 | E-4-[2-methyl-2-(1,1,4,4-tetra-methyl-6-isopropyl-1,2,3,4-tetrahydronaphth-7-yl)-vinyl]-N—(tetrazol-5-yl)-benzamide |
| 43 | —$CH_2$— | —$CH_3$ | —$CH_3$ | H | —$CH_3$ | 279–280 | E | 17.64 | E-4-[2-methyl-(1,1,3,3-tetra-methylindan-6-yl)-vinyl]-N—tetrazol-5-yl)-benzamide |
| 44 | —$CH_2$—$CH_2$— | —$CH_3$ | $CH_3$ | —$CH_2$—CH(CH$_3$)$_2$ | $CH_3$ | 280 | E | | E-4-[2-methyl-2-(1,1,4,4-tetra-methyl-6-(2-methylpropyl-1,2,3,4-tetrahydronaphth-7-yl-vinyl]-N—(tetrazol-5-yl)-benzamide |

We claim:
1. A phenylethylene derivative of the formula

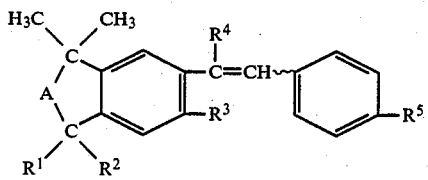

where A is $C_1$–$C_2$-alkylene which is unsubstituted or substituted by methyl, $R^1$ is hydrogen or methyl, $R^2$ is hydrogen or methyl, $R^3$ is $C_1$–$C_8$-alkyl, $R^4$ is hydrogen or $C_1$–$C_4$-alkyl and $R^5$ is carboxyl or $C_2$–$C_4$-carbalkoxy, and, where relevant, its salts with physiologically tolerated bases.

2. A phenylethylene derivative of the formula I as set forth in claim 1, where A is ethylene, $R^1$ and $R^2$ are each methyl, $R^3$ is $C_1$–$C_{16}$-alkyl, $R^4$ is methyl and $R^5$ is carboxyl or $C_2$–$C_4$-carboalkoxy, and its salts with physiologically tolerated bases.

3. A phenylethylene derivative of the formula I as set forth in claim 1, where A is ethylene, $R^1$ and $R^2$ are each methyl, $R^3$ is $C_1$–$C_{12}$-alkyl, $R^4$ is methyl and $R^5$ is carboxyl or $C_2$–$C_2$-carboalkoxy, and its salts with physiologically tolerated bases.

4. A phenylethylene derivative of the formula I as set forth in claim 1, where A is ethylene, $R^1$ and $R^2$ are each methyl, $R^3$ is $C_1$–$C_8$-alkyl, $R^4$ is methyl and $R^5$ is carboxyl or $C_2$–$C_4$-carboalkoxy, and its salts with physiologically tolerated bases.

5. A phenylethylene derivative of the formula I as set forth in claim 1, wherein A is ethylene, $R^1$, $R^2$ and $R^4$ are methyl, $R^3$ is 2-methyl-propyl, $R^5$ is carboxyl, with E-configuration.

6. A phenylethylene derivative of the formula I as set forth in claim 1, wherein A and $R^1$ through $R^4$ are the same as described in claim 7, and $R^5$ is —$COOC_2H_5$.

7. A phenylethylene derivative of the formula I as set forth in claim 1, wherein A and $R^1$ through $R^4$ are the same as described in claim 7, and $R^5$ is —$COOCH_3$.

8. A phenylethylene derivative of the formula I as set forth in claim 1, wherein A is methylene, $R^1$, $R^2$ and $R^4$ are methyl, $R^3$ is 2-methyl-propyl and $R^5$ is carboxyl.

9. A drug containing a compound of the formula I as set forth in claim 1.

10. A therapeutic agent comprising a pharmaceutical carrier and an effective amount of a compound of the formula I as set forth in claim 1 as the active compound.

11. A phenylethylene derivative of the formula I as set forth in claim 1, wherein A is ethylene, $R^1$–$R^4$ are methyl and $R^5$ is COOH.

* * * * *